United States Patent [19]

Laptewicz, Jr.

[11] Patent Number: 5,071,040
[45] Date of Patent: Dec. 10, 1991

[54] SURGICAL ADHESIVES MIXING AND DISPENSING IMPLEMENT

[75] Inventor: Joseph E. Laptewicz, Jr., Stonington, Conn.

[73] Assignee: Pfizer Hospital Products Group, Inc., New York, N.Y.

[21] Appl. No.: 491,754

[22] Filed: Mar. 9, 1990

[51] Int. Cl.⁵ ............................................. G01F 11/00
[52] U.S. Cl. .................................. 222/235; 222/260; 222/390; 366/196; 604/218; 606/93
[58] Field of Search ........ 222/136, 137, 229, 233–235, 222/260, 278, 280, 390; 206/219; 366/194–196, 186, 247, 249, 251; 604/82, 218, 224, 228; 606/92, 93

[56] References Cited

U.S. PATENT DOCUMENTS

| | | | |
|---|---|---|---|
| 1,391,325 | 9/1921 | Killian | 222/390 |
| 3,013,697 | 12/1961 | Gill | 222/135 |
| 3,028,052 | 4/1962 | Archer | 222/136 |
| 3,140,078 | 7/1964 | Krahe et al. | 259/47 |
| 3,153,531 | 10/1964 | Cook | 259/113 |
| 3,164,303 | 1/1965 | Trautmann | 222/190 |
| 3,373,906 | 3/1968 | De Hart et al. | 222/235 |
| 3,417,971 | 12/1968 | Blank et al. | 366/196 |
| 4,189,065 | 2/1980 | Herold | 222/390 X |
| 4,277,184 | 7/1981 | Solomon | 366/150 |
| 4,671,263 | 6/1987 | Draemert | 128/92 VO |
| 4,810,249 | 3/1989 | Haber et al. | 222/390 X |
| 4,906,231 | 3/1990 | Young | 604/228 X |
| 4,952,065 | 8/1990 | Kreuziger | 366/247 X |
| 4,973,168 | 11/1990 | Chan | 206/219 X |

Primary Examiner—Michael S. Huppert
Assistant Examiner—Gregory L. Huson
Attorney, Agent, or Firm—Peter C. Richardson; Lawrence C. Akers; Raymond W. Augustin

[57] ABSTRACT

An apparatus for mixing and dispensing a surgical adhesive having at least two components has a barrel with a central longitudinal axis extending from a first to a second end thereof. The second end includes a nozzle with a discharge port. A rotatable screw conveyor shaft extends through the barrel position along the longitudinal axis. A dispensing element is mounted within the barrel and has a threaded bore for operative engagement with the screw shaft. The dispensing element has a keyway and may freely rotate at the first end of the barrel. A snap element is included to move the dispensing element into engagement with a key on the inner surface of the barrel which prevents the rotation of the dispensing element and causes the dispensing element to move from the first end of the barrel to the second end dispensing the adhesive.

18 Claims, 3 Drawing Sheets

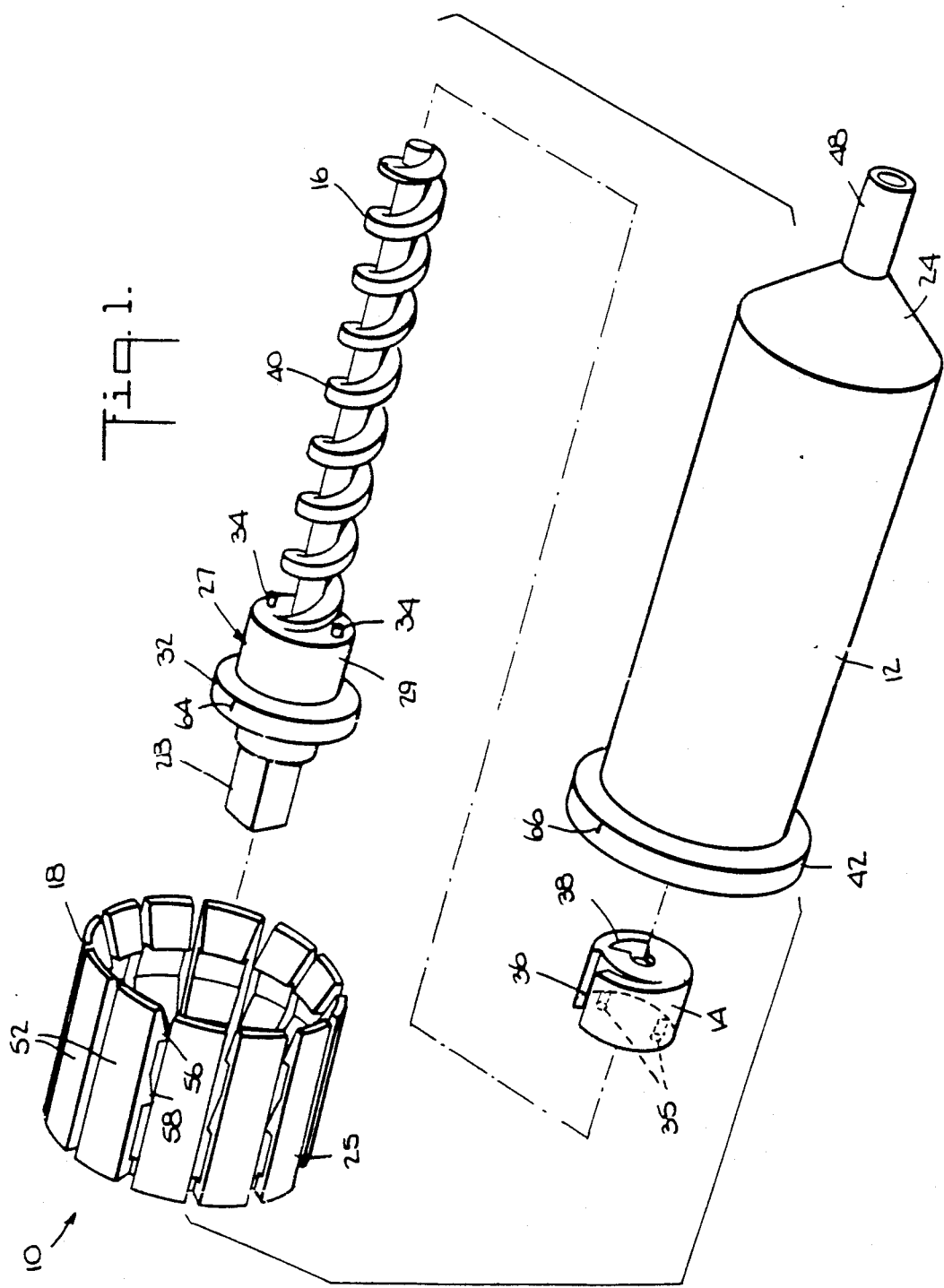

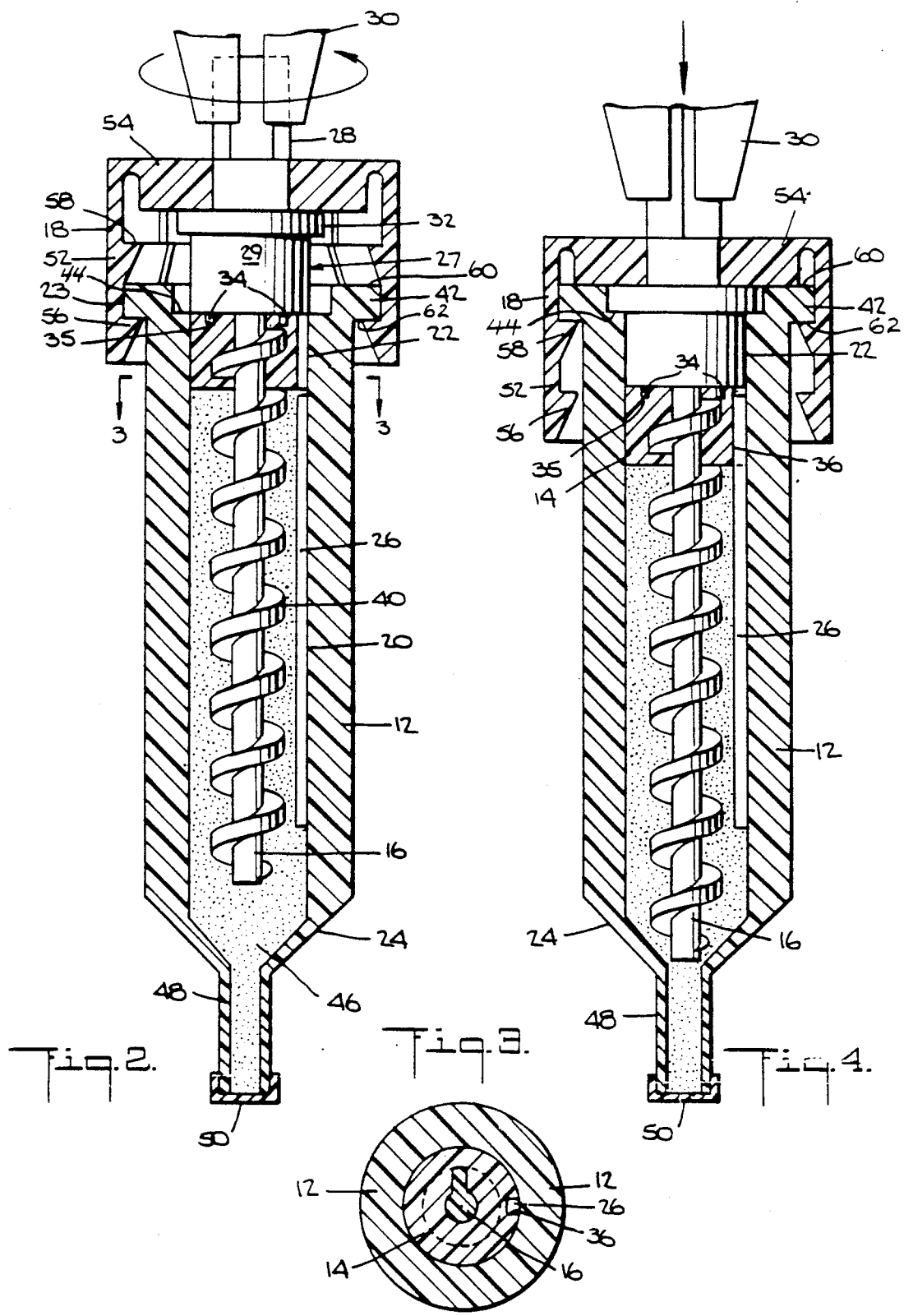

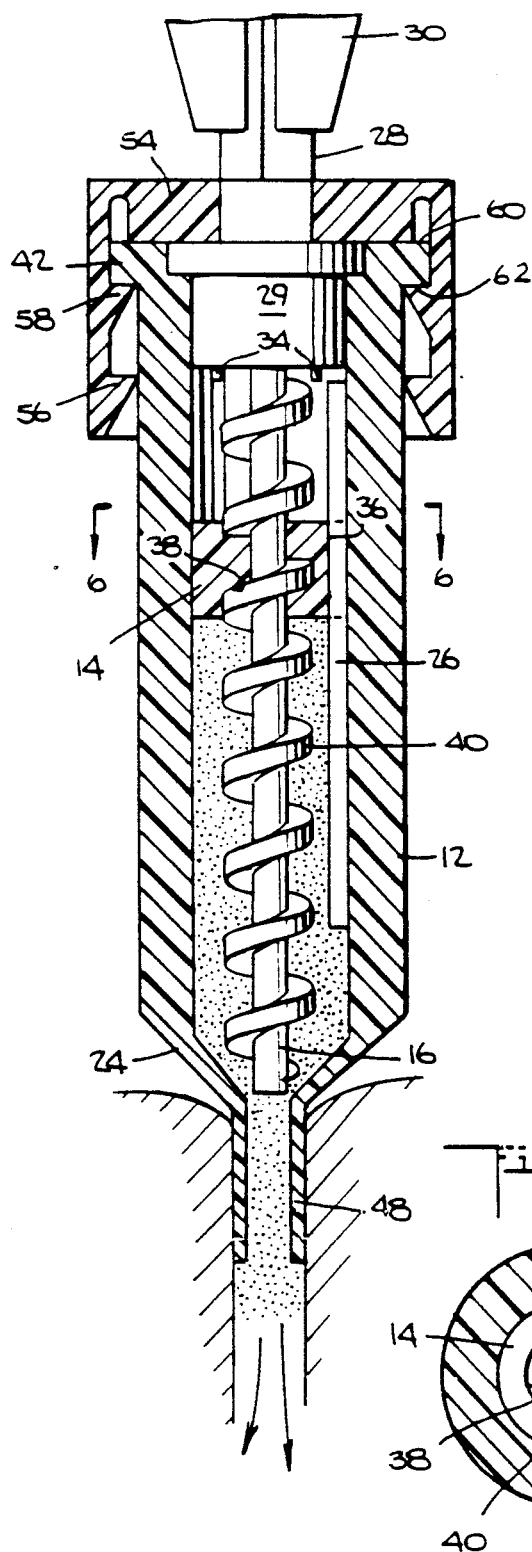
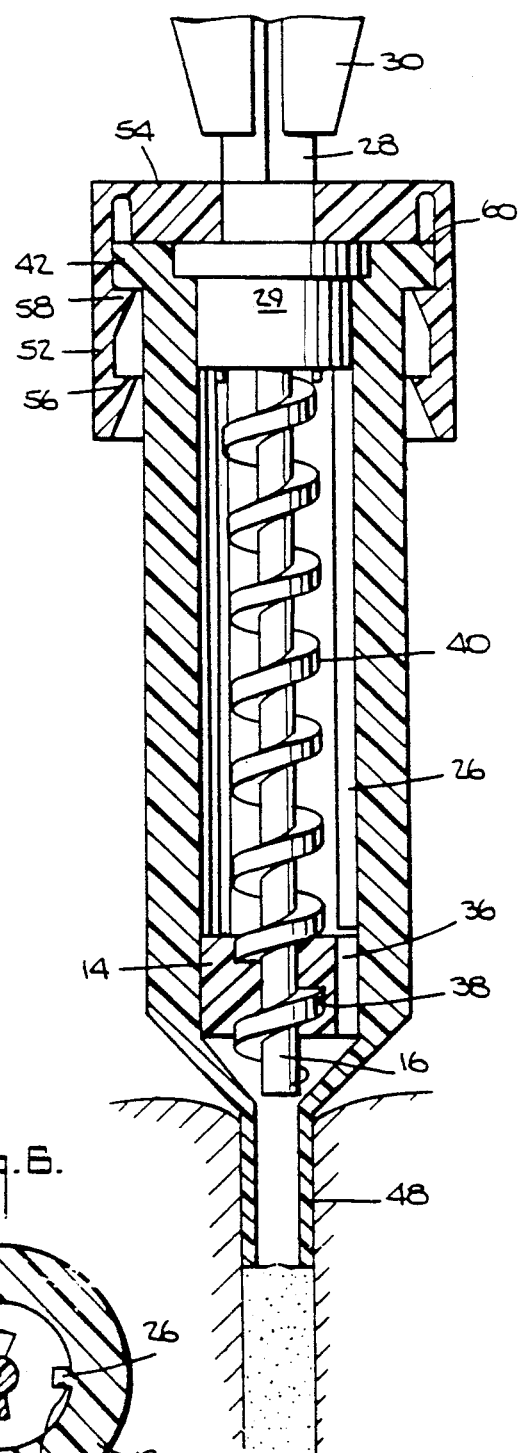
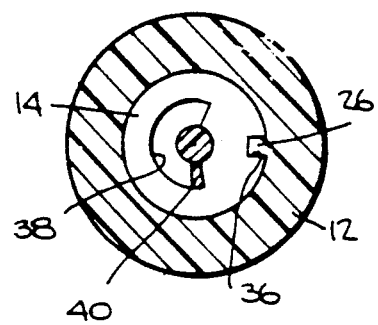

SURGICAL ADHESIVES MIXING AND DISPENSING IMPLEMENT

BACKGROUND OF THE INVENTION

1. Field of the Invention

The present invention relates to the preparation, mixing and application of multi-component surgical adhesives. More particularly, the present invention relates to an implement for mixing and applying adhesives or bone cements used in orthopedic surgery to seat and secure metal or plastic prostheses into living bone. Typically, such bone cement is prepared just prior to use as a mixture of a liquid monomer such as methylmethacrylate and a powdered copolymer. The mixture is then injected as a viscous fluid into the surgical sight and is then polymerized insitu and in vivo to provide a solid implantation.

2. Description of the Prior Art

Various implements have been designed and utilized to mix and dispense surgical adhesives, such as bone cements, during surgery. For example, U.S. Pat. No. 4,277,184 which issued to Solomon on July 7, 1981, relates to a disposable orthopaedic implement in which two adhesive components are mixed in a closed system, under vacuum, with the aid of a mixing element. The mixing element can be extended during mixing and retracted during the dispensing operation.

U.S. Pat. No. 4,671,263, which issued on June 9, 1987 to Klaus Draenert, discloses a device for mixing and applying a polymethylmethacrylate bone cement under a constant pressure.

Various other United States patents disclose devices for storing and dispensing multi-component compositions. Such devices are shown in U.S. Pat. Nos. 3,028,052, 3,153,531, 3,013,697, 3,140,078 and 3,164,303. For example, U.S. Pat. No. 3,013,697, which issued on Dec. 19, 1961 to W. Gill, discloses a mixing and dispensing device for mixing liquid and powdered products and thereupon immediately dispensing the same. This device contains first and second tubes, each adapted to contain one part of a two-component system. The device, however, does not disclose any means to mix the two components once they are combined.

A disadvantage with all the devices disclosed above is that when mixing a multi-component adhesive which includes both liquid and powdered components, quick and adequate mixing is very difficult when done by hand. To alleviate this problem, electrically or pneumatically powdered mixers have been employed so that quick and thorough mixing of the multi-part components can be accomplished. This is especially important when, as is the case with polymethylmethacrylate bone cements, the adhesive must be used quickly prior to polymerization of the mixture.

In an operating room setting it is undesirable to first mix the multi-component surgical adhesives and then transfer these components into a separate device for application. Not only is such a process time consuming, but it also increases the risk of contaminating the mixing area and application area with particles of adhesives.

Consequently, there has been a long-felt need to provide a mixing and dispensing apparatus which can be electrically or pneumatically powered, which can quickly mix a multi-component adhesive, and which can quickly dispense the mixed adhesive without requiring disassembly and reassembly of parts and without requiring the surgeon to leave the immediate area of the operation. The mixing and dispensing apparatus of the present invention allows for the quick, powered mixing of a multi-component adhesive and the powered dispensing of the same with the surgeon having only to do minor manipulations of the device.

SUMMARY OF THE INVENTION

It is an object of the invention to provide an apparatus into which the components of a multi-component adhesive can be placed and quickly mixed and dispensed with a minimum of assembly and disassembly of the apparatus.

It is yet another object of the invention to provide an apparatus for mixing and dispensing surgical adhesives which is easily adaptable to powered mixing and dispensing.

It is still yet a further object of the invention to provide a mixing and dispensing apparatus in which the transition from a mixing mode to a dispensing mode can be accomplished with only minor manipulations of the apparatus by the user.

These and related objects are achieved in the present invention by an apparatus for mixing and dispensing surgical adhesives having at least two components. The apparatus includes a first barrel portion of predetermined cross-section having a central longitudinal axis extending therethrough from a first to a second end thereof. The barrel includes a second barrel portion fixedly attached to the first end of the first barrel portion and coaxial therewith.

A rotatable screw-shaped mixing element extends through the first and second barrel portions along the longitudinal axis. A rotatable drive element adapted to be driven by either an electric or pneumatic power device is operatively coupled to the mixing element adjacent the second barrel portion. A dispensing element is located in the second barrel portion and is engagable with and is rotatable with the drive element. The dispensing element has a cross-section substantially identical to the predetermined cross-section of the first barrel portion.

The dispensing element has a threaded central opening therein for receiving and operatively engaging the screw-shaped mixing element. The dispensing element rotates along with the screw-shaped mixing element when disposed within the second portion of the barrel. The apparatus includes a snap element mounted adjacent to the end of the second barrel portion opposite the end attached to the first end of the first barrel portion and is operatively connected to the dispensing element. The snap element operatively engages the dispensing element to move it from a first position wherein the dispensing element is in the second barrel portion and is engaging said driver element to a second position wherein the dispensing element is moved from the second barrel portion into the first barrel portion.

Complimentary keys and keyways are provided on the outer surface of the dispensing element and the inner surface of the first barrel portion. The interaction of the key, either on the dispensing element or the inside circumference of the first barrel portion, in a complimentary keyway, on either the respective dispensing element or the inner circumference of the first barrel portion, prevents the relative rotation of the dispensing element within the first barrel portion. Because the threaded central opening in the dispensing element includes threads corresponding to the threads on the screw shaft, rotation of the screw shaft causes the dispensing element to move axially along the screw shaft from the first end to a second end of the first barrel portion. This movement forces the mixed surgical adhesive out a discharge port in the second end of the first barrel portion.

The apparatus further includes a removable cap for selectively opening and closing the discharge port at the second end of the first barrel portion. The second end of the first barrel portion may be in the form of a nozzle with the discharge port located at the converging end thereof. The nozzle area may be configured to help force the adhesive back from the second barrel end toward the first barrel end along the periphery of the barrel circumference during the mixing operation. The removable cap which sealingly engages the end of the nozzle is closed during the mixing operation and then opened or removed during the dispensing operation. A sealing element, such as an O-ring, may be used to further seal the interface between the rotatable drive element and the second barrel portion.

These and other objects and advantages of the present invention will become apparent from the following description of the accompanying drawings, which disclose one embodiment of the invention. It is to be understood that the drawings are to be used for the purposes of illustration only, and not as a definition of the invention.

BRIEF DESCRIPTION OF THE DRAWINGS

In the drawings wherein similar reference characters denote similar elements throughout the several views:

FIG. 1 is an exploded view, in isometric form, of the mixing and dispensing apparatus of the present invention;

FIG. 2 is an elevation view of the apparatus of the present invention partially in cross-section with the dispensing element in the mixing position;

FIG. 3 is a cross-sectional view along lines 3—3 of FIG. 2;

FIG. 4 is a side view of the apparatus of the present invention partially in cross-section with the dispensing element in the dispensing position;

FIG. 5 is a side view of the apparatus of the present invention partially in cross-section showing the dispensing element mid-way in the dispensing operation;

FIG. 6 is a cross-sectional view of FIG. 5 along line 6—6; and

FIG. 7 is a side view of the apparatus of the present invention partially in cross-section with the dispensing element in its final position.

DESCRIPTION OF THE PREFERRED EMBODIMENT

Referring to FIGS. 1-7, there is shown the mixing and dispensing apparatus of the present invention generally denoted as 10. Apparatus 10 includes a cylindrical barrel portion 12, a cylindrical dispensing element 14, a rotatable screw shaft 16 and a snap element 18.

Barrel 12 has two portions 20 and 22. First barrel portion 20 extends for almost the entire length of barrel 12 with second barrel portion 22 adjacent to a first end 23 of the barrel opposite a second or discharge end 24. Second barrel portion 22 has an axial length sufficient to accommodate the axial length of dispensing element 14. Discharge end 24 of barrel 12 is preferably in the shape of a nozzle 46 leading to a dispensing tube 48. Tube 48 may be selectively sealed or opened via the insertion or removal of a cap 50. (Nozzle 46 may be shaped to force the adhesive from dispensing end 24 back towards end 23 of barrel 12 during the mixing operation when cap 50 seals tube 48.) This insures complete mixing of the components of the adhesive.

Both second barrel portion 22 and discharge end 24 are sized to allow dispensing element 14 to rotate freely therein. A key 26 extends along the inner circumference of first barrel portion 20 and may be located at any convenient circumferential position therearound. As described below, key 26 is designed to prevent dispensing element 14 from freely rotating when in first barrel portion 20.

Screw shaft 16 is axially aligned within barrel portions 20 and 22 for rotation therein. At the end of screw shaft 16, adjacent to first end 23 of barrel 12, there is formed a rotatable drive element 27 which is operatively coupled to screw shaft 16 or formed integrally therewith and has at its end disposed adjacent barrel portion 22, a cylindrical plug 29 for sealing end 23 of barrel 12. Rotatable drive element 27 also includes a coupling shaft 28, which preferably can be either square or in the form of a hex and is designed for coupling to a pneumatically or electrically powered drive device partially shown as 30. Drive element 27 also includes cap portion 32 which is integrally formed with and caps plug 29. The end of plug 29 opposite cap 32 includes pins 34 which loosely engage corresponding bores 35 in dispensing element 14. Pins and bores 34, 35 keep dispensing element 34 rotating with shaft 16 and drive element 27 when in barrel portion 22.

In the preferred embodiment, screw shaft 16 is in the form of a screw conveyor capable of moving the multicomponent adhesive from the first end 23 of barrel 12 to dispensing end 24. The screw conveyor is designed to both transport the adhesive and to cause movement of dispensing element 14 therealong. The diameter and the pitch of the threads 40 on screw shaft 16 is adapted to be received within a threaded central bore 38 inside dispensing element 14 having an identical diameter and pitch. The diameter and pitch are chosen to efficiently mix the adhesive and move dispensing element 14 along screw shaft 16 in the dispensing mode. In order to facilitate mixing, the diameter of the screw can be sized at 75% of the diameter of barrel 12. For liquid/liquid systems, this relative dimension can be adjusted depending on relative viscosity of the components. This allows recirculation of the adhesive during mixing.

Dispensing element 14 includes a complimentary keyway 36 for receiving key element 26 upon movement of dispensing element 14 from second barrel portion 22 into first barrel portion 20. Since dispensing element 14 has a threaded bore 38 corresponding to the threads or flights 40 on screw shaft 16, dispensing element 14 may be threaded up and down screw shaft 16.

Snap element 18 is designed to snap over and engage a flange portion 42 of barrel 12 at end 23 thereof. Flange portion 42 includes a shallow bore 44 concentric with the longitudinal axis of barrel 12. Bore 44 is adapted to receive cap portion 32 of drive element 27.

In the preferred embodiment, snap element 18 is in the form of a hollow cap comprised of a multiplicity of individual deflecting elements 52, each joined at the top to end piece 54. Each deflecting element 52 includes two inwardly extending ledges 56 and 58 respectively. All the ledges 56, 58 are adapted to slide over the top surface 60 of flange portion 42 and engage the bottom surface 62 thereof. As can be seen in FIGS. 2 and 4, ledge 56 is engaging step portion 42 when apparatus 10 is in the mixing mode, with ledge 58 engaging step portion 42 when apparatus 10 is in the dispensing mode.

An alignment system is provided so that key 36 may be aligned with keyway 26 so that dispensing element 14 may be moved from second barrel portion 22 to first barrel portion 20. This system may simply consist of an alignment guide or marking 64 on cap 32 of drive element 27. Guide 64 is aligned with keyway 36 on dispensing element 14 when bores 35 are placed onto pins 34. Obviously, the pins and bores 34, 35 are originally oriented so that this may occur. The outside of barrel 12 also has an alignment guide or marking 66 aligned with key 26 formed within barrel portion 20. Thus guides 64, 66 may be aligned so that dispensing element 14 may be moved from barrel portion 22 into barrel portion 20 with the mating of key 26 and keyway 36.

Referring again to FIGS. 1-7, the operation of the mixing and dispensing apparatus will now be described. Initially, the user takes empty barrel portion 12 and ensures that cap 50 seals the opening of nozzle tube 48. He then adds the components of the multi-component adhesive to be mixed into the barrel 12 and then inserts into end 23 of barrel 12 an assembly comprising screw shaft 16, drive element 27, dispensing element 14 mounted to drive element 27, with pins 34 engaging corresponding bores 35. Snap element 18 is then placed over step portion 42 of barrel portion 12, such that ledges 56 are engaging underside 62 of step portion 42 as shown in FIG. 2. At this point; dispensing element 14 is situated within second barrel portion 22 which permits the free rotation of dispensing element 14.

Driver 30 is then coupled to drive shaft 28 and screw shaft 16 is rotated. It has been found that rotational speeds of between 10-20 revolutions per minute produces adequate mixing of typical solid/liquid multi-component systems, whereas higher speeds may be suitable for liquid/liquid systems. After mixing for an adequate time, usually several minutes, the alignment guide 64 on cap 32 must be aligned with the alignment marker 66 on the outside of barrel 12 to ensure that keyway 36 on dispensing element 14 is aligned with key 26 on the inner circumference of barrel 12 along first portion 20 thereof. This operation, of course, must be done with drive 30 stopped.

Once the complimentary keyways are aligned, the user grasps snap element 18 and moves it axially downwardly such that ledge element 58 snaps over step element 42 and engages bottom surface 62 thereof. Dispensing element 14 is then prevented from rotating by the interaction of key 26 and keyway 36. It is then able to be pulled off of pins 34 of drive element 27 upon the rotation of screw shaft 16. The drive 30 is again turned on and is rotated at a slow speed so that dispensing element 14 is moved axially in the downward direction as shown in FIGS. 5 and 7 until it disengages key 26 and resides in discharge end 24 of barrel 12.

Referring to FIG. 7, it can be seen that when dispensing element 14 is at its lower most point within end 24 of barrel 12, keyway 22 is again disengaged from key 20 so that the dispensing element is again free to rotate along with screw shaft 16 and therefore without producing any further downward force which could damage the device. This is accomplished by simply stopping the key 26 a sufficient distance prior to nozzle portion 46 to accommodate the axial length of dispensing element 14.

It can also be seen that, if desired, the key portion may be placed on dispensing element 14 and the keyway may be formed within first barrel portion 20. Then in both discharge area 24 and in second barrel portion 22 there must be an enlarged diameter to accommodate the free rotation of dispensing element 14 inside barrel 12 with a key extending outwardly therefrom.

In addition, while loosely engaging pins 34 and bore 35 are used to ensure that dispensing element 14 rotates along with screw shaft 16 when located in the second barrel portion 22, the dispensing element may be held in a fixed position relative to drive element 27 in any other suitable manner. This can be accomplished in any manner so long as the dispensing element rotates freely as the screw shaft rotates. It should also be noted that the diameter and pitch of the screws or flights 40 of screw conveyor shaft 16 may be designed to facilitate mixing of the specific components contemplated. These dimensions would be optimized depending on the various viscosities of adhesive mixtures.

While one example of the present invention has been described, it is obvious that many changes and modifications may be made thereunto, without departing from the spirit and scope of the invention.

What is claimed is:

1. An apparatus for mixing an dispensing multi-component adhesives comprising;
    a barrel having a central longitudinal axis extending from a first end to a second end thereof;
    a discharge port at said second end of said barrel portion;
    a rotatable screw shaft extending through said barrel along said central longitudinal axis, said screw shaft rotatably supported within said barrel at said first end of said barrel, said rotatable screw shaft is in the form of a screw conveyor for transporting the mixed adhesive along said central longitudinal axis from said first end to said second end of said barrel;
    a dispensing element rotatably mounted within the first end of said barrel and having a threaded central opening therein receiving and engaging said screw shaft; and
    a means for selectively operatively engaging said dispensing element with a means for preventing the rotation of said dispensing element with said screw shaft to effect relative movement thereof from said first to said second end of said barrel upon rotation of said screw shaft.

2. The apparatus as set forth in claim 1 wherein said dispensing element having a threaded central opening therein includes threads having a pitch equal to that of said threads of said screw conveyor.

3. The apparatus as set forth in claim 2 wherein the screw conveyor has a predetermined diameter and pitch which facilitates mixing of the adhesive components.

4. The apparatus as set forth in claim 1 further including a means for selectively opening and closing said discharge port.

5. The apparatus as set forth in claim 4 wherein said means for selectively opening and closing said discharge port is a removable cap.

6. The apparatus as set forth in claim 1 wherein said second end of said barrel is in the form of a nozzle with said discharge port located at the converging end thereof.

7. The apparatus as set forth in claim 6 further including a removable cap for sealingly engaging the end of said nozzle so that the discharge port may be selectively opened or closed.

8. The apparatus as set forth in claim 1 wherein said barrel has a first barrel portion of predetermined cross-section and a second portion located at said first end of said barrel. wherein said dispensing element has a cross-section substantially equal to said predetermined cross-section of said first barrel portion.

9. The apparatus as set forth in claim 8 wherein said means for preventing the rotation of said dispensing element is located within said first barrel portion.

10. The apparatus as set forth in claim 9 wherein said means for preventing rotation of said dispensing element in said first barrel portion includes a key on one of an outer circumference of said dispensing element or on an inner surface of said barrel and a complimentary keyway formed on one of said outer circumference of said dispensing element or said inner surface of said first barrel portion.

11. The apparatus set forth in claim 10 further including a rotatable drive element operatively coupled to said screw shaft for supporting said screw shaft and wherein said dispensing element is engagable and rotatable with said drive element.

12. The apparatus as set forth in claim 11 wherein said means for selectively operatively engaging said dispensing element with said screw shaft is a snap element mounted adjacent to said first end of said barrel and operatively connected thereto, said snap element operatively engaging said dispensing element and is movable from a first position wherein said dispensing element is in said second barrel portion and is engaging said drive element to a second position wherein said dispensing element is moved into said first barrel portion and engaging one of said key or said keyway.

13. The apparatus as set forth in claim 11 wherein said barrel includes a third barrel portion adjacent the second end thereof, and wherein said dispensing element is freely rotatable in said second and third barrel portions.

14. The apparatus as set forth in claim 11 wherein said drive element includes a means for sealing said first end of said barrel.

15. An apparatus for mixing and dispensing an adhesive having at least two components, comprising:
- a barrel portion having a central longitudinal axis extending therethrough;
- a discharge port at one end of said barrel portion;
- a rotatable screw-shaped mixing element extending through said barrel portion along said central longitudinal axis;
- a dispensing element having a threaded bore selectively operatively engagable with said screw-shaped mixing element for axial movement therealong upon the rotation thereof; and
- a means located at an end of said barrel opposite said one end for selectively operatively engaging said dispensing element with said rotatable screw-shaped mixing element affecting axial movement of said dispensing element along said screw-shaped mixing element towards said discharge port.

16. An apparatus for mixing and dispensing a multicomponent adhesive comprising;
- a first barrel of predetermined cross-section having a central longitudinal axis extending therethrough from a first to a second end thereof;
- a second barrel portion fixedly attached to the first end of said first barrel portion and coaxial therewith and having a cross-section larger than the predetermined cross-section of said first barrel portion;
- a rotatable screw-shaped mixing element extending through said barrel along said central longitudinal axis;
- a rotatable drive element sealing the first end of said barrel operatively coupled to said mixing element;
- a dispensing element engagable with and rotatable with said drive element and having a cross-section substantially identical to said predetermined cross-section of said barrel and having a threaded central opening therein receiving and operatively engaging said screw-shaped mixing element, said dispensing element rotatable with said screw-shaped mixing element in a first position within said barrel;
- a means associated with said first end of said barrel for selectively moving said dispensing element out of engagement with said drive element into a second position within said barrel; and
- a means for preventing the rotation of said dispensing element when in said second position so that said dispensing element is moved along said mixing element from said first end to said second end of said barrel by the rotation thereof.

17. The apparatus as set forth in claim 16 wherein said means for preventing rotation of said dispensing element includes a key on one of an outer circumference of said dispensing element or on an inner surface of said barrel and a respective complimentary key way formed on one of said outer circumference of said dispensing element or said inner surface of said barrel.

18. The apparatus as set forth in claim 16 wherein said means for selectively moving said dispensing element out of engagement with said drive element and into said second position is a snap element mounted adjacent to said first end of said barrel and operatively connected thereto, said snap element operatively engaging said dispensing element and is movable from a first position wherein said dispensing element is in said first position engaging said drive element to a second position wherein said dispensing element is moved into said second position.

* * * * *